United States Patent
Lund et al.

(10) Patent No.: US 10,729,052 B1
(45) Date of Patent: Aug. 4, 2020

(54) SYSTEM AND METHOD FOR MEASURING SOIL CONDUCTIVITY USING EXISTING FARM IMPLEMENTS

(71) Applicant: Veris Technologies, Inc., Salina, KS (US)

(72) Inventors: Eric Lund, Salina, KS (US); Paul Drummond, Minneapolis, KS (US); Kyle Jensen, Salina, KS (US); Chase Maxton, Salina, KS (US)

(73) Assignee: Veris Technologies, Inc., Salina, KS (US)

( * ) Notice: Subject to any disclaimer, the term of this patent is extended or adjusted under 35 U.S.C. 154(b) by 196 days.

(21) Appl. No.: 15/862,459

(22) Filed: Jan. 4, 2018

Related U.S. Application Data

(60) Provisional application No. 62/445,237, filed on Jan. 11, 2017.

(51) Int. Cl.
| | |
|---|---|
| *A01B 49/04* | (2006.01) |
| *A01B 33/12* | (2006.01) |
| *A01G 25/16* | (2006.01) |
| *G01N 33/24* | (2006.01) |

(Continued)

(52) U.S. Cl.
CPC ............ *A01B 33/12* (2013.01); *A01G 25/167* (2013.01); *A01B 79/005* (2013.01); *A01C 21/007* (2013.01); *G01N 2033/245* (2013.01)

(58) Field of Classification Search
CPC ............ A01B 49/04; G01N 2033/245; G01N 27/043; G01N 2001/021; G01N 33/24; G01N 33/245; G01N 33/246
See application file for complete search history.

(56) References Cited

U.S. PATENT DOCUMENTS

| | | |
|---|---|---|
| 3,084,553 A | 4/1963 | Cullinan et al. |
| 3,224,512 A | 12/1965 | Alexander |
| 3,331,249 A | 7/1967 | Boxrud |

(Continued)

OTHER PUBLICATIONS

Adamchuk et al., "On-the-go soil sensors for precision agriculture", Computers and Electronics in Agriculture, No. 44, pp. 71-91, Jun. 12, 2004.

(Continued)

*Primary Examiner* — Matthew Troutman
(74) *Attorney, Agent, or Firm* — Jefferson L. Thompson; Thompson Law, P.A.

(57) ABSTRACT

A system for measuring soil properties on-the-go uses soil-engaging components of an existing farm implement as electrodes for a soil conductivity measurement system. The soil-engaging components can be: electrically isolated shanks and/or replaceable points or sweeps on a tillage implement; a row cleaner or coulter device on the front of a planter row unit, the closing wheels on the back of the planter row unit, or an entire planter row unit; or an additional soil contacting component added to an existing implement shank. A soil engaging component serving as an electrode is electrically isolated from other components of the implement. A soil conductivity measurement is made by passing current between a first pair of soil-engaging electrodes and measuring voltage resulting from the current between a second pair of soil-engaging electrodes. A narrow profile sensor unit can be attached to the implement to measure additional soil properties.

21 Claims, 19 Drawing Sheets

(51) Int. Cl.
*A01C 21/00* (2006.01)
*A01B 79/00* (2006.01)

(56) References Cited

U.S. PATENT DOCUMENTS

| | | | |
|---|---|---|---|
| 3,464,504 A | 9/1969 | Stange | |
| 3,593,809 A | 7/1971 | Derry | |
| 3,625,296 A | 12/1971 | Mabry | |
| 3,774,237 A | 11/1973 | Hardway, Jr. | |
| 4,191,263 A | 3/1980 | Malterer | |
| 4,316,393 A | 2/1982 | Philipenko | |
| RE30,901 E | 4/1982 | Boxrud | |
| 4,332,301 A | 6/1982 | Jonell | |
| 4,333,541 A | 6/1982 | Doty | |
| 4,482,021 A | 11/1984 | Repski | |
| 4,531,087 A | 7/1985 | Larson | |
| 4,534,231 A | 8/1985 | Jonsson et al. | |
| 5,021,939 A | 6/1991 | Pulgiese | |
| 5,033,397 A * | 7/1991 | Colburn, Jr. | A01B 79/005 111/118 |
| 5,076,372 A | 12/1991 | Hellbusch | |
| 5,211,248 A | 5/1993 | Nosewicz et al. | |
| 5,394,949 A | 3/1995 | Wright et al. | |
| 5,435,399 A | 7/1995 | Peterson et al. | |
| 5,524,560 A * | 6/1996 | Carter | A01B 63/114 111/200 |
| 5,673,637 A * | 10/1997 | Colburn, Jr. | A01B 79/005 111/118 |
| 5,741,983 A | 4/1998 | Skotnikov et al. | |
| 5,841,282 A | 11/1998 | Christy et al. | |
| 5,887,491 A | 3/1999 | Monson et al. | |
| 5,950,741 A | 9/1999 | Wright et al. | |
| 6,016,713 A | 1/2000 | Hale | |
| 6,116,172 A | 9/2000 | Prairie et al. | |
| 6,138,590 A * | 10/2000 | Colburn, Jr. | A01B 79/005 111/118 |
| 6,237,429 B1 | 5/2001 | Melnyk | |
| 6,260,633 B1 | 7/2001 | Machek et al. | |
| 6,360,829 B1 | 3/2002 | Naber et al. | |
| 6,363,803 B1 | 4/2002 | Hubers | |
| 6,484,652 B1 * | 11/2002 | Colburn, Jr. | A01B 79/005 111/118 |
| 6,592,820 B1 | 7/2003 | Hardman et al. | |
| 6,766,865 B1 | 7/2004 | Dagel et al. | |
| 6,959,245 B2 | 10/2005 | Rooney et al. | |
| 6,975,245 B1 | 12/2005 | Slater et al. | |
| 7,216,555 B2 | 5/2007 | Drummond et al. | |
| 7,255,016 B2 | 8/2007 | Burton | |
| 7,552,654 B2 | 6/2009 | Burton | |
| 7,827,873 B2 | 11/2010 | Burton | |
| 8,204,689 B2 * | 6/2012 | Christy | A01B 79/005 702/28 |
| 8,451,449 B2 | 5/2013 | Holland | |
| 8,573,074 B2 | 11/2013 | Marker | |
| 9,113,589 B2 * | 8/2015 | Bassett | A01C 7/205 |
| 9,285,501 B2 * | 3/2016 | Christy | G01N 21/359 |
| 2002/0131046 A1 | 9/2002 | Christy et al. | |
| 2003/0016029 A1 | 1/2003 | Schuler et al. | |
| 2004/0052686 A1 | 3/2004 | Hardman et al. | |
| 2005/0034437 A1 | 2/2005 | McMurtry et al. | |
| 2005/0172733 A1 | 8/2005 | Drummond et al. | |
| 2005/0279163 A1 | 12/2005 | Chesk | |
| 2006/0114006 A1 | 6/2006 | Mohamed | |
| 2007/0068238 A1 | 3/2007 | Wendte | |
| 2007/0151467 A1 | 7/2007 | Furll et al. | |
| 2008/0199359 A1 | 8/2008 | Davis et al. | |
| 2009/0112475 A1 * | 4/2009 | Christy | A01B 79/005 702/5 |
| 2010/0275565 A1 | 11/2010 | Moe et al. | |
| 2011/0106451 A1 | 5/2011 | Christy et al. | |
| 2011/0203356 A1 | 8/2011 | Scherbring | |
| 2012/0048160 A1 | 3/2012 | Adams et al. | |
| 2012/0089304 A1 | 4/2012 | Hamilton et al. | |
| 2012/0091222 A1 | 4/2012 | Dresselhaus et al. | |
| 2012/0130552 A1 | 5/2012 | Schmidt et al. | |
| 2013/0046446 A1 | 2/2013 | Anderson | |
| 2013/0191073 A1 | 7/2013 | Rice et al. | |
| 2013/0250305 A1 | 9/2013 | Holland | |
| 2013/0325267 A1 | 12/2013 | Adams et al. | |
| 2014/0116735 A1 | 5/2014 | Bassett | |
| 2014/0303854 A1 | 10/2014 | Zielke | |

OTHER PUBLICATIONS

Fares et al., "Improved Calibration Functions of Three Capacitance Probes for the Measurement of Soil Moisture in Tropical Soils", Sensors, No. 11, pp. 4858-4874, May 3, 2011.

\* cited by examiner

_Fig. 13_
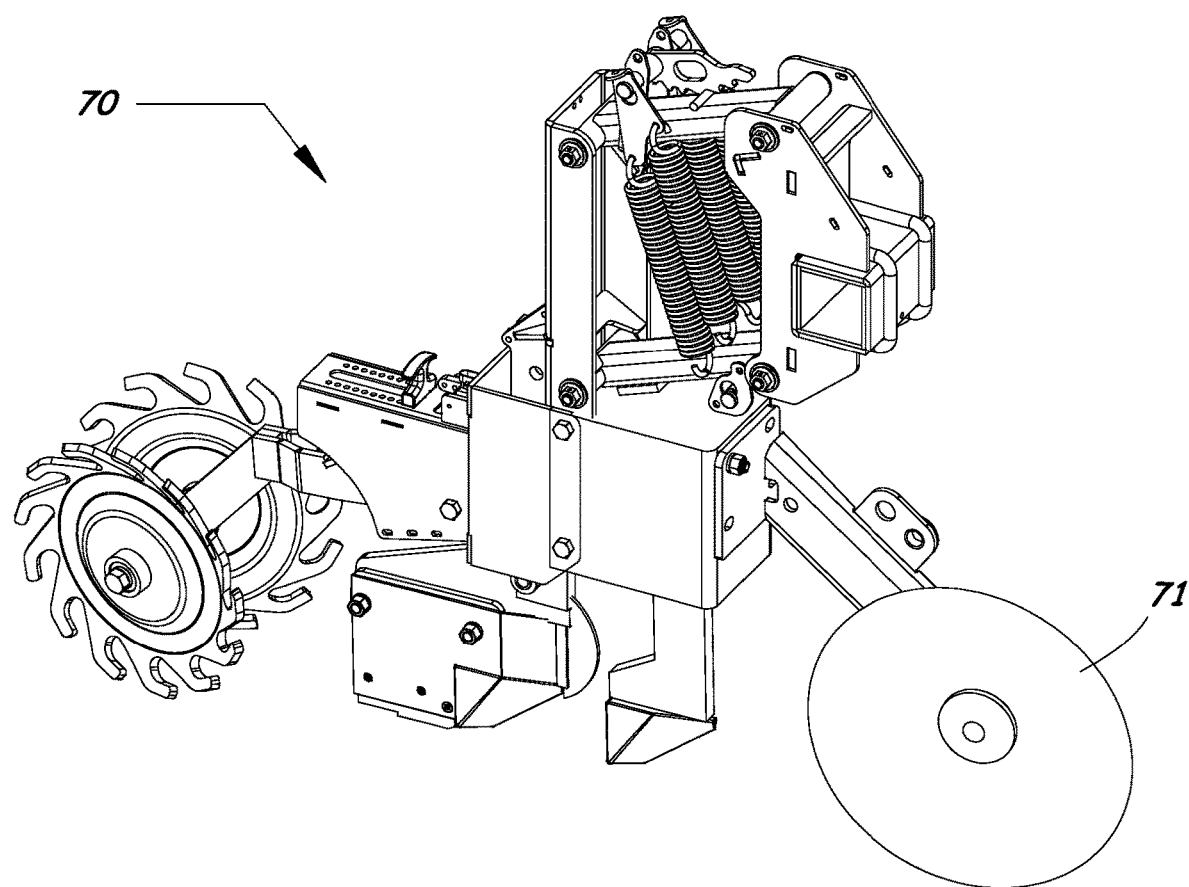

SYSTEM AND METHOD FOR MEASURING SOIL CONDUCTIVITY USING EXISTING FARM IMPLEMENTS

RELATED APPLICATIONS

This application claims the benefit of U.S. Provisional Patent Application No. 62/445,237 filed on Jan. 11, 2017. This application also relates to the subject matter of U.S. Provisional Patent Application Nos. 61/812,131 and 62/216,087, and U.S. Utility patent application Ser. Nos. 15/261,825, 14/253,304 and 14/253,839. The entire contents of these related applications are incorporated herein by reference.

BACKGROUND OF THE INVENTION

Field of the Invention

The present invention relates generally to methods and systems for measuring and mapping soil properties across a field, and more particularly to a system and method for measuring soil properties on-the-go using existing farm implements.

Description of the Related Art

Soil texture and organic matter are major factors driving crop productivity. Prior art devices exist to measure these properties using electrical conductivity and optical sensing. For example, U.S. Pat. No. 5,841,282 issued to Christy et al. discloses a device for measuring soil conductivity that uses an array of coulters to measure soil conductivity at multiple soil depths in a single pass.

However, previously developed devices are bulky and require mounting on a stand-alone implement frame. Pulling those devices requires a unique, separate pass through the field for data collection. The extra pass through the field is an added cost, and the seasonal window to make the measurements is narrow.

Soil moisture is another major factor driving crop productivity, particularly in arid regions. Soil moisture varies spatially within fields due to soil texture, topography, crop usage, irrigation patterns, and various other variables.

Fixed, semi-permanent moisture sensors (e.g., gypsum blocks and neutron probes) and manually inserted sensors (e.g., TDR, capacitance) have been used for many years to monitor soil moisture levels in agricultural fields. However, these moisture sensors do not capture the spatial variability as their expense and manual deployment make it unfeasible to collect enough measurements to produce a spatially accurate map of soil moisture.

Variable rate irrigation allows limited irrigation water supplies to be applied at different rates in different areas of a field. For example, variable rate irrigation can be used to apply more irrigation water to zones of a field where water holding capacity is lower or where crop use or productivity is expected to be greater. Fixed moisture sensors are often used in fields with variable rate irrigation. However, the use of fixed moisture sensors does not link soil moisture with soil properties that affect water-holding capacity and crop usage of water.

Soil pH and other chemical properties are also important factors for crop productivity. Mapping soil pH and other chemical properties is typically done with laboriously collected lab samples, or with a tractor-drawn implement, such as the Veris on-the-go system (pH). However, it is not feasible to map soil pH or other chemical properties at a high density using conventionally collected lab samples, and the cost of a Veris on-the-go system for such mapping measurements is sometimes too expensive.

There is a need for a method and system for on-the-go measurement of multiple soil properties using a narrow profile sensor configuration.

SUMMARY OF THE INVENTION

An object of the present invention is to provide a method and system for on-the-go measurement of soil properties that uses existing soil-engaging components of farm implements, such as planters and tillage tools, as electrodes.

A further object of the present invention is to provide a method and system for on-the-go measurement of soil properties that measures soil electrical conductivity using classic multiple electrode arrays.

A further object of the present invention is to provide a system for on-the-go measurement of soil properties that can be mounted on an existing implement, such as a planter, fertilizer applicator, or tillage implement.

A further object of the present invention is to provide a method and system for on-the-go measurement of soil properties that allows a dense mapping of multiple soil properties with a relatively low total investment.

A further object of the present invention is to provide a system for on-the-go measurement of soil properties that uses existing soil-engaging components on an implement as electrodes for measuring soil electrical conductivity at a relatively deep depth, and has a narrow profile sensor unit mounted to the implement to collect soil electrical conductivity, soil optical, soil moisture, and/or soil pH simultaneously at a relatively shallow depth.

To accomplish these and other objects of the invention, a system and method are provided for measuring soil properties on-the-go using soil-engaging components of an existing farm implement as electrodes for a soil conductivity measurement system. The soil-engaging components can be: electrically isolated shanks and/or replaceable points or sweeps on a tillage implement, such as a field cultivator; a row cleaner or coulter device on the front of a planter row unit, the closing wheels on the back of a planter row unit, or an entire planter row unit; or an additional soil contacting component added to an existing implement shank. A soil engaging component serving as an electrode of the soil conductivity measurement system is electrically isolated from other components of the implement. A soil conductivity measurement is made by passing current between a first pair of soil-engaging electrodes and measuring voltage resulting from the current between a second pair of soil-engaging electrodes. A narrow profile sensor unit can also be attached to the implement to measure additional soil properties, such as soil temperature, soil reflectance, soil moisture, and soil pH.

According to one aspect of the present invention, an agricultural implement having a secondary function of measuring soil conductivity is provided, comprising: a frame or toolbar adapted to be conveyed over a ground surface; a plurality of soil-engaging components mounted to the frame or toolbar, the soil-engaging components being spaced across a width of the implement to provide a tillage, planting or fertilizing function; first and second pairs of soil-engaging electrodes mounted to or integral with corresponding first and second pairs of the soil-engaging components, the second pair of electrodes being arranged between and aligned with the first pair of electrodes, the first and second pairs of electrodes being electrically insulated from each other and from the frame; and a soil conductivity measurement system that passes a current between the first pair of soil-engaging electrodes through the soil and measures a voltage resulting from the current between the second pair of soil-engaging electrodes to determine soil conductivity.

Numerous other objects of the present invention will be apparent to those skilled in this art from the following description wherein there is shown and described embodiments of the present invention, simply by way of illustration of some of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings:

FIG. 13 is a front perspective view of a narrow profile sensor unit according to another embodiment of the present invention.

DETAILED DESCRIPTION OF THE INVENTION

A method and system for measuring multiple soil properties according to the present invention will now be described in detail with reference to FIGS. 1 to 19 of the accompanying drawings.

Figure 1:
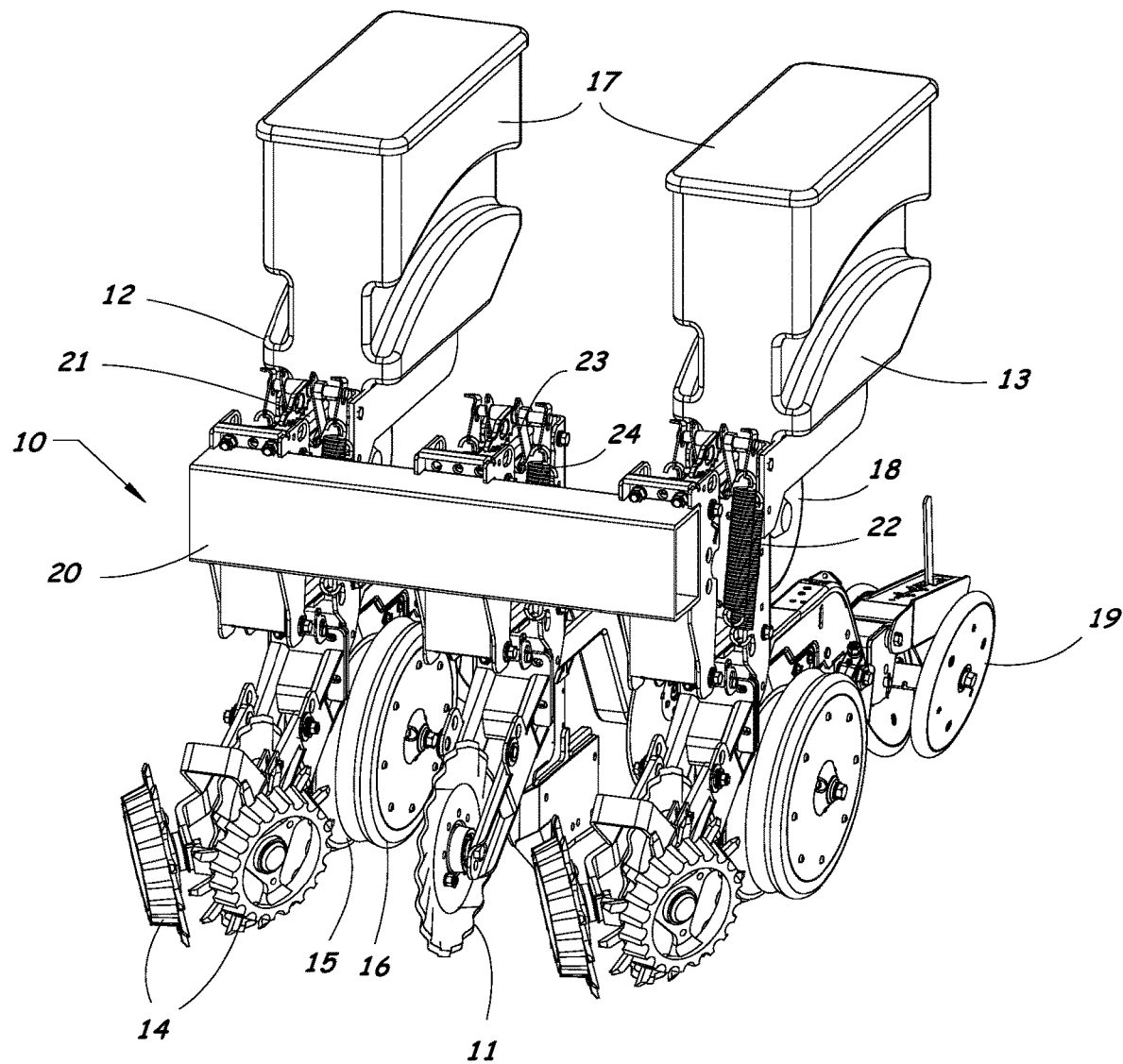
FIG. 1 is a front perspective view of a row crop implement equipped with a narrow profile sensor unit positioned between two adjacent row units.
Figure 2:
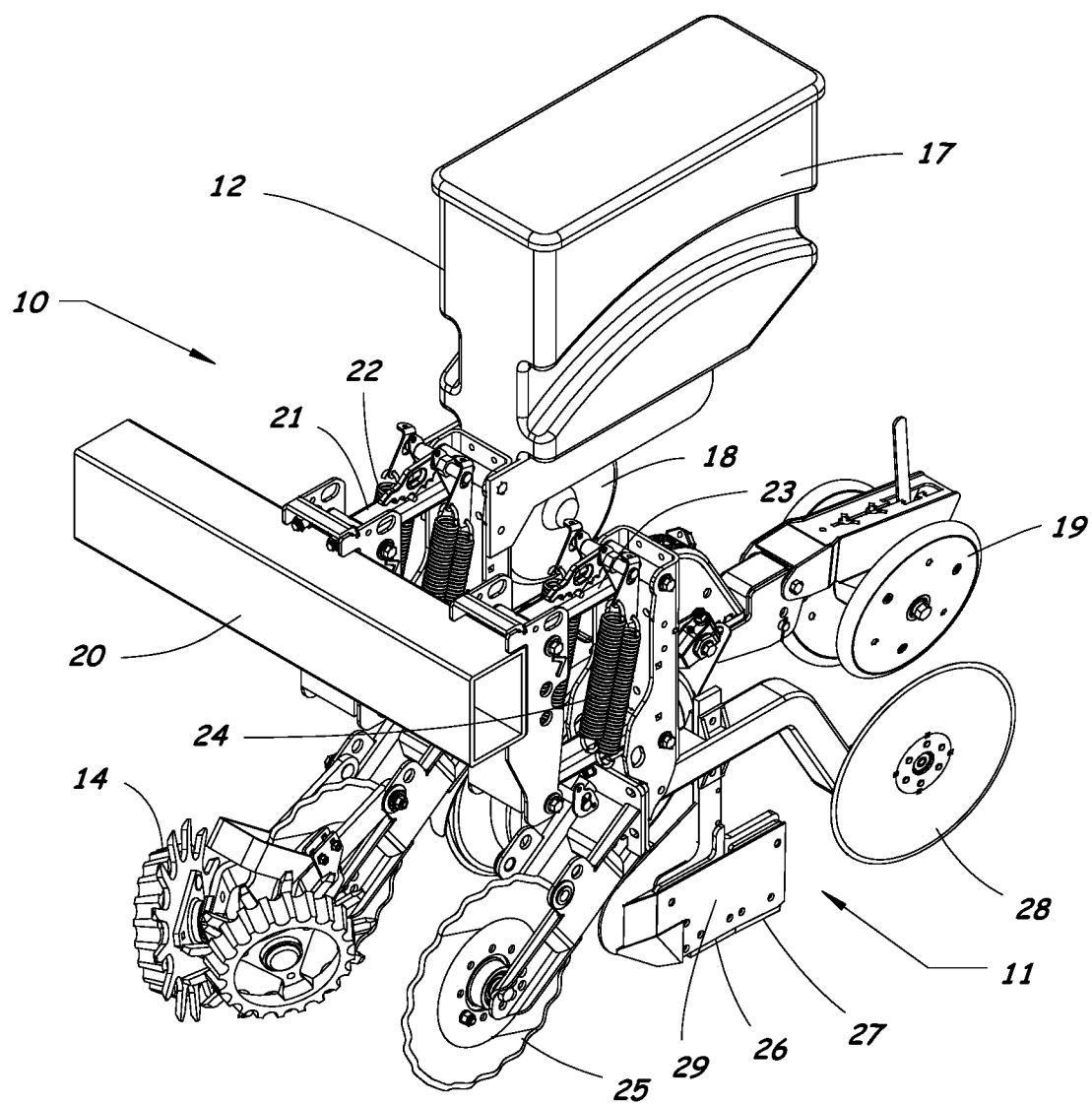
FIG. 2 is another front perspective view of the row crop implement with one of the row units removed to illustrate the narrow profile sensor unit of the present invention.
Figure 3:
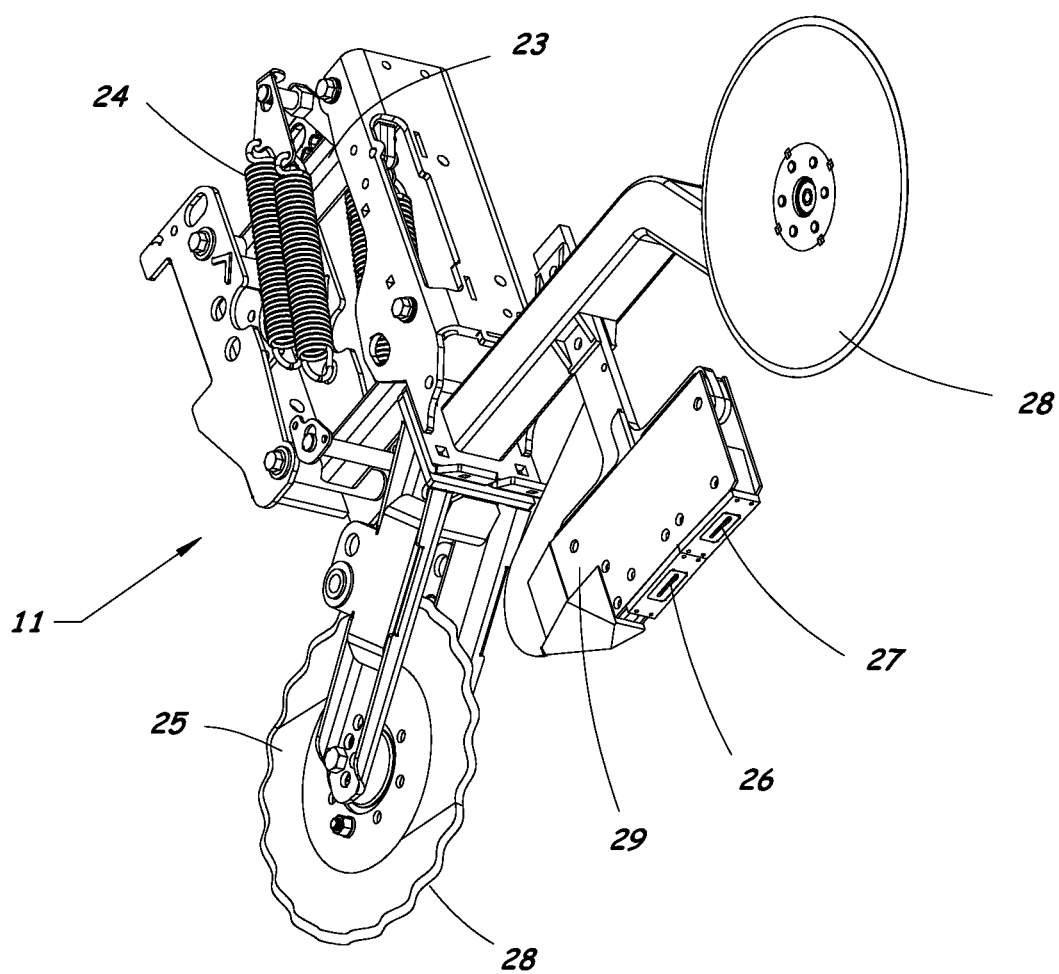
FIG. 3 is a lower left side perspective view of the narrow profile sensor unit according to a first embodiment of the present invention.
Figure 4:
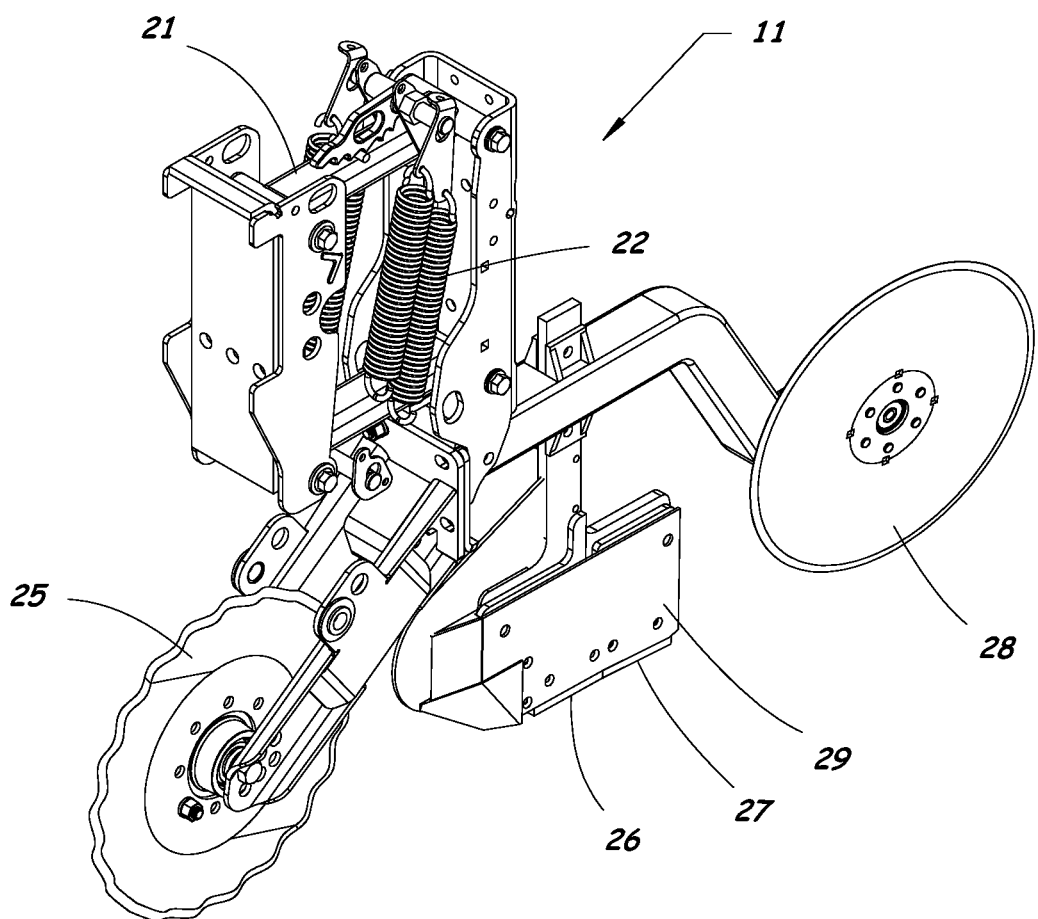
FIG. 4 is a front perspective view of the narrow profile sensor unit shown in FIG. 3.
Figure 5:
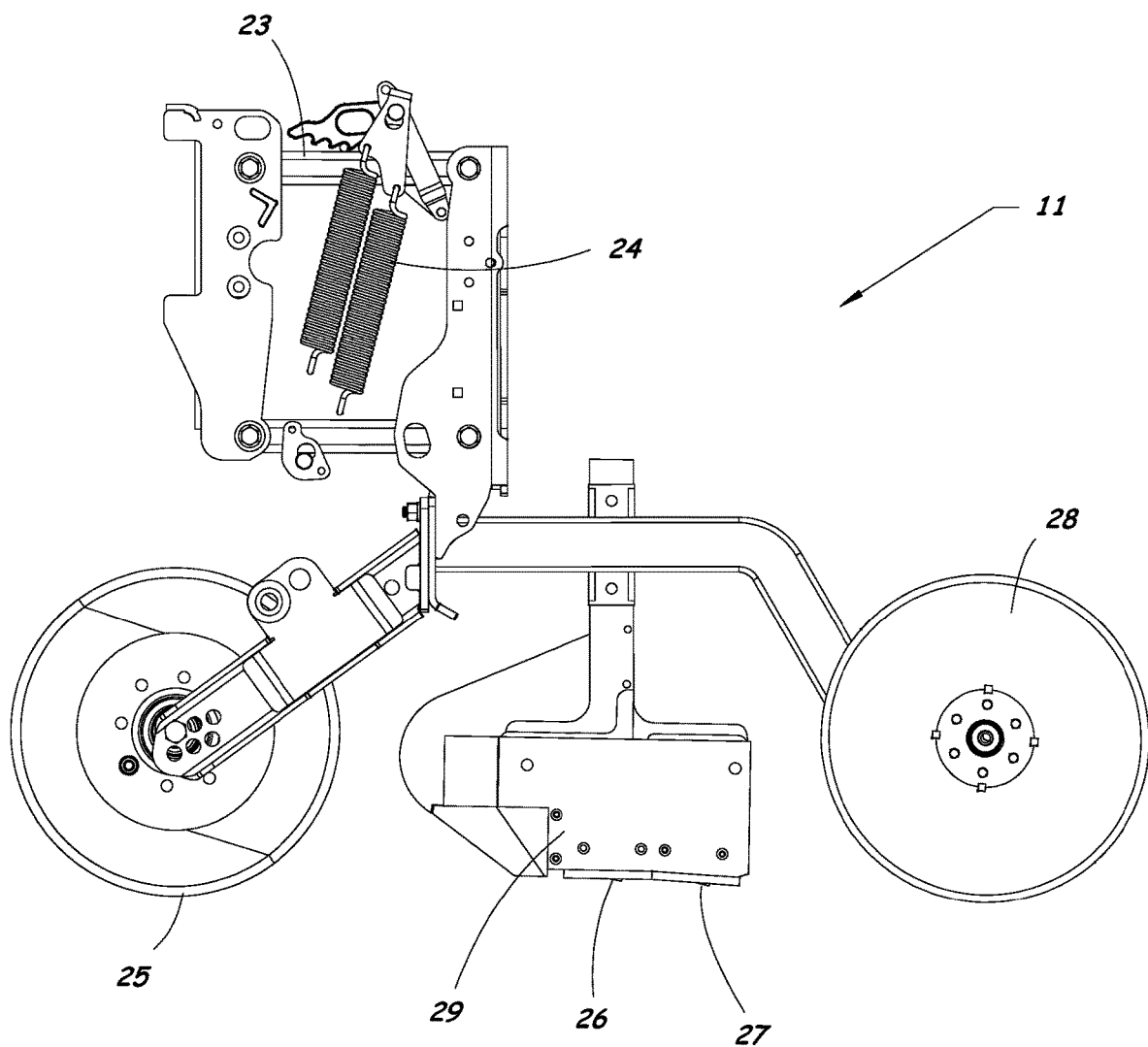
FIG. 5 is a side elevation view of the narrow profile sensor unit shown in FIG. 3.

FIGS. 1 and 2 illustrate a row crop implement 10 equipped with a narrow profile sensor unit 11 according to the present invention. The narrow profile sensor unit 11 is positioned between two adjacent row units 12, 13 of the implement 10. The row units 12, 13 can be planter row units, as shown in FIGS. 1 and 2. Alternatively, the row units can be conventional strip tillage units or fertilizer applicator row units, which are attached to an implement tool bar.

The planter row units 12, 13 each have a row clearing assembly 14 for moving crop residue and debris to the sides of the row, a furrow opener assembly 15 with gauge wheels 16 for opening a furrow in the soil, a seed hopper 17, a seed metering mechanism 18 for dropping seeds through a seed tube into the furrow, and a furrow closing assembly 19. The row units 12, 13 are attached to a planter tool bar 20 by parallel linkage assemblies 21. Springs 22 are attached to the parallel linkage assemblies 21 to transfer additional down pressure from the toolbar 20 to the row units 12, 13.

The narrow profile sensor unit 11 is attached to the same tool bar 20 as the conventional row units 12, 13 using a similar parallel linkage assembly 23 and springs 24 for transferring additional down pressure from the toolbar 20 to the sensor unit 11. This allows the implement 10 to be used for its original purpose of planting, tilling or fertilizing, as well as for measuring various properties of the soil in the field. The soil property measurements using the narrow profile sensor unit 11 can thus be made in conjunction with a farming pass already being made in the field.

Alternatively, the narrow profile sensor unit 11 can be installed on a light-duty frame for pulling with an ATV-type vehicle in a separate pass over the field. Conventional systems for measuring soil conductivity typically have each electrode of a four electrode array cutting its own path in the soil. The in-line design of the narrow profile sensor unit 11 of the present invention results in a lower draft requirement as compared to such conventional systems.

The narrow profile sensor unit 11 includes a first soil engaging component 25, a second soil engaging component 26, a third soil engaging component 27, and a fourth soil engaging component 28. The first, second, third and fourth soil engaging components 25, 26, 27, 28 are arranged substantially in-line with each other so that the second, third and fourth soil engaging components 26, 27, 28 follow directly behind the first soil engaging component 25 during forward movement of the implement through the field. By using soil engaging components 25-28 that are substantially aligned with each other in a direction of travel, the draft requirement for the sensor unit 11 is reduced and the sensor unit 11 can be made more compact.

The first soil engaging component 25 is a rotating disk or coulter arranged to open a slot in the soil. The second and third soil engaging components 26, 27 are attached to the bottom of a runner 29 arranged to follow behind the first soil engaging component 25 for sliding contact with the soil in the slot created by the first soil engaging component 25. The fourth soil engaging component 28 is a rotating disk or spoked wheel arranged to follow behind the runner 26 to close the slot.

In the embodiment shown in FIGS. 1 to 5, the first, second, third and fourth soil engaging components 25-28 of the narrow profile sensor unit 11 provide a four electrode array for measuring soil electrical conductivity. The electrode array includes the first soil engaging component 25 functioning as the first electrode for contacting the soil. The second and third soil engaging components 26, 27 attached to the bottom of the runner 29 function as the second and third electrodes of the electrode array. The second and third soil engaging components 26, 27 each have an angled leading edge that projects below the bottom surface of the runner 29 and slopes downwardly and rearwardly to provide better soil contact. The fourth soil engaging component 28 functions as the fourth electrode of the electrode array.

The electrode array can be a Wenner or Schlumberger array with the first and fourth electrodes 25, 28 connected to a source of electrical current to inject electrical current into the soil, and the second and third electrodes 26, 27 connected to a voltage measuring circuit to measure the voltage drop in the injected electrical current from the first and fourth electrodes 25, 28.

Figure 6:
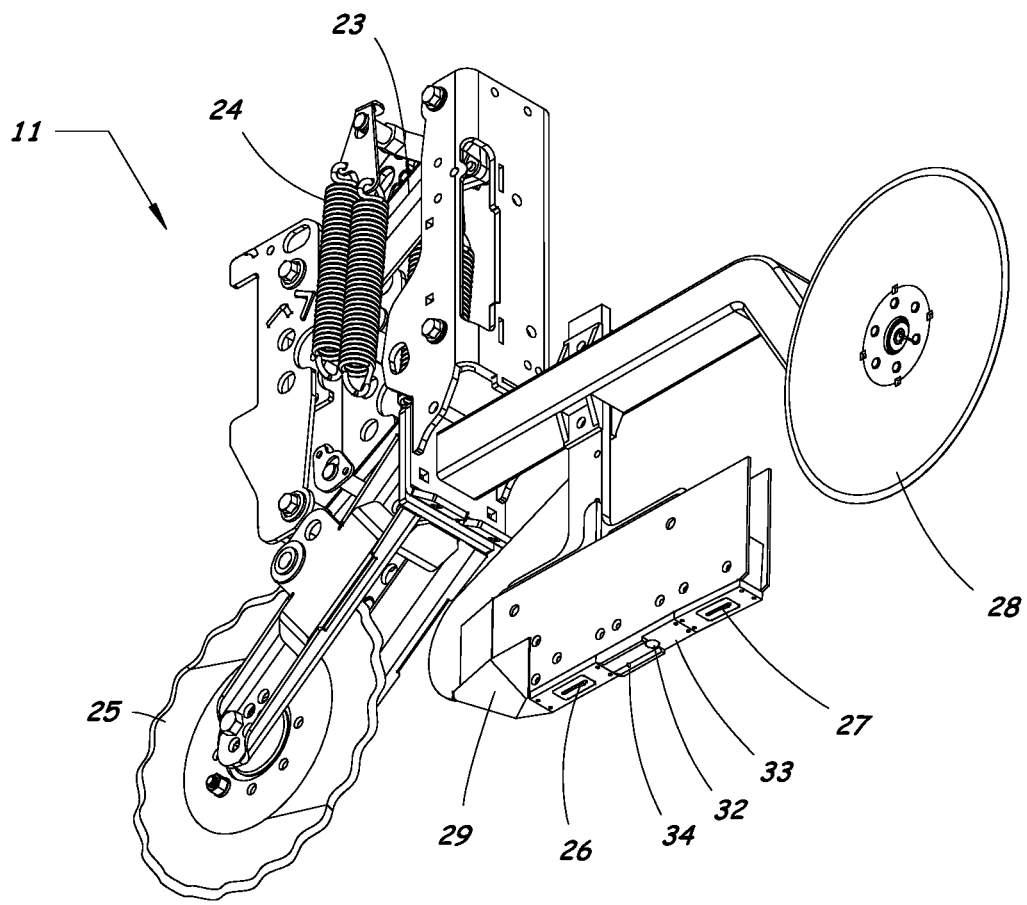
FIG. 6 is a lower left side perspective view of a narrow profile sensor unit with an optical window positioned in the lower surface of the runner between two embedded electrodes according to a second embodiment of the present invention.

The narrow profile sensor unit 11 can be equipped with other sensors for measuring soil properties. As shown in FIG. 6, the runner 29 can be made with an optical window 32 in the lower soil engaging surface 33 between the second and third electrodes 26, 27. A sensor for measuring optical reflectance of the soil through the optical window 32 is contained within the runner 29. A pair of protective fins 34 are positioned on right and left sides of the optical window 32 and protrude from the runner 29 below a lower surface of the optical window 32 for protecting the window 32 during use.

Figure 7:
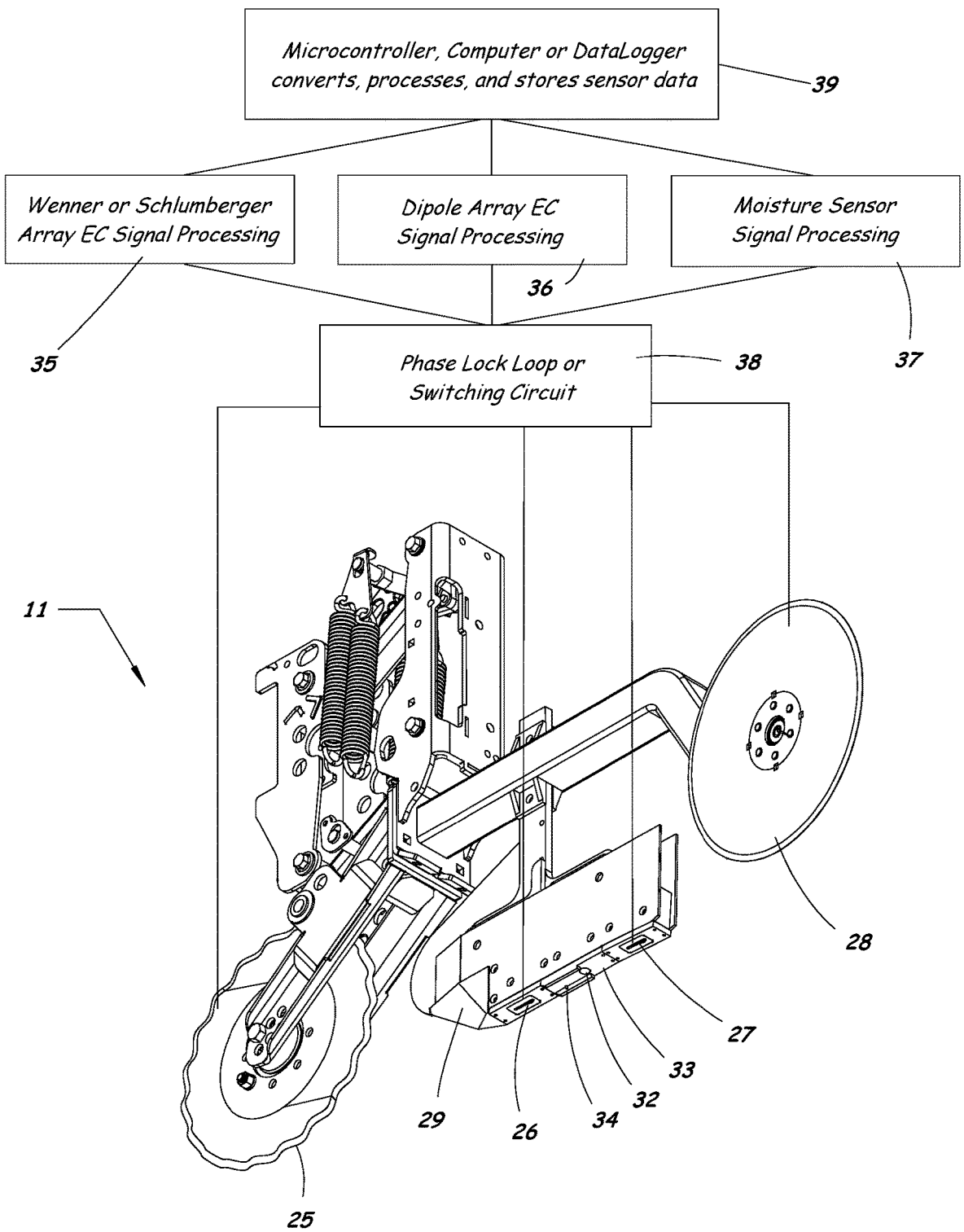
FIG. 7 is a lower left side perspective view of the narrow profile sensor unit shown in FIG. 6, with a diagram illustrating the various signal processing circuits that can be used with the sensor unit to detect multiple soil properties.

As shown in FIG. 7, the narrow profile sensor unit 11 can be equipped with multiple signal processing circuits to measure a plurality of soil properties using the same soil engaging components 25-28. A first signal processing circuit 35 is provided for using the electrode array 25-28 as a Wenner or Schlumberger array for measuring soil electrical conductivity at a relatively deep depth (e.g., 1 to 3 feet). A second signal processing circuit 36 is provided for using the electrode array as a dipole array for measuring soil electrical conductivity at a relatively shallow depth (e.g., less than 12 inches). A third signal processing circuit 37 (e.g., a capacitance circuit) is provided for using two electrodes 26, 27 of the electrode array to measure and generate a soil moisture signal.

A phase lock loop or a switching circuit 38 is provided between the electrodes 25-28 and the first, second and third signal processing circuits 35-37 to allow the signal processing circuits 35-37 to measure soil electrical conductivity at both the deep and shallow depths, as well as soil moisture, using the same electrode array 25-28. For example, the phase lock loop can be used to differentiate the four electrode array signal from the dipole signal, or the switching circuit can be used to rapidly switch between the signal processing circuits 35-37. The signal processing circuits 35-37 are connected to a micro controller, computer or data logger 39 to convert, process and store the sensor data received from the signal processing circuits 35-37.

Figure 8:
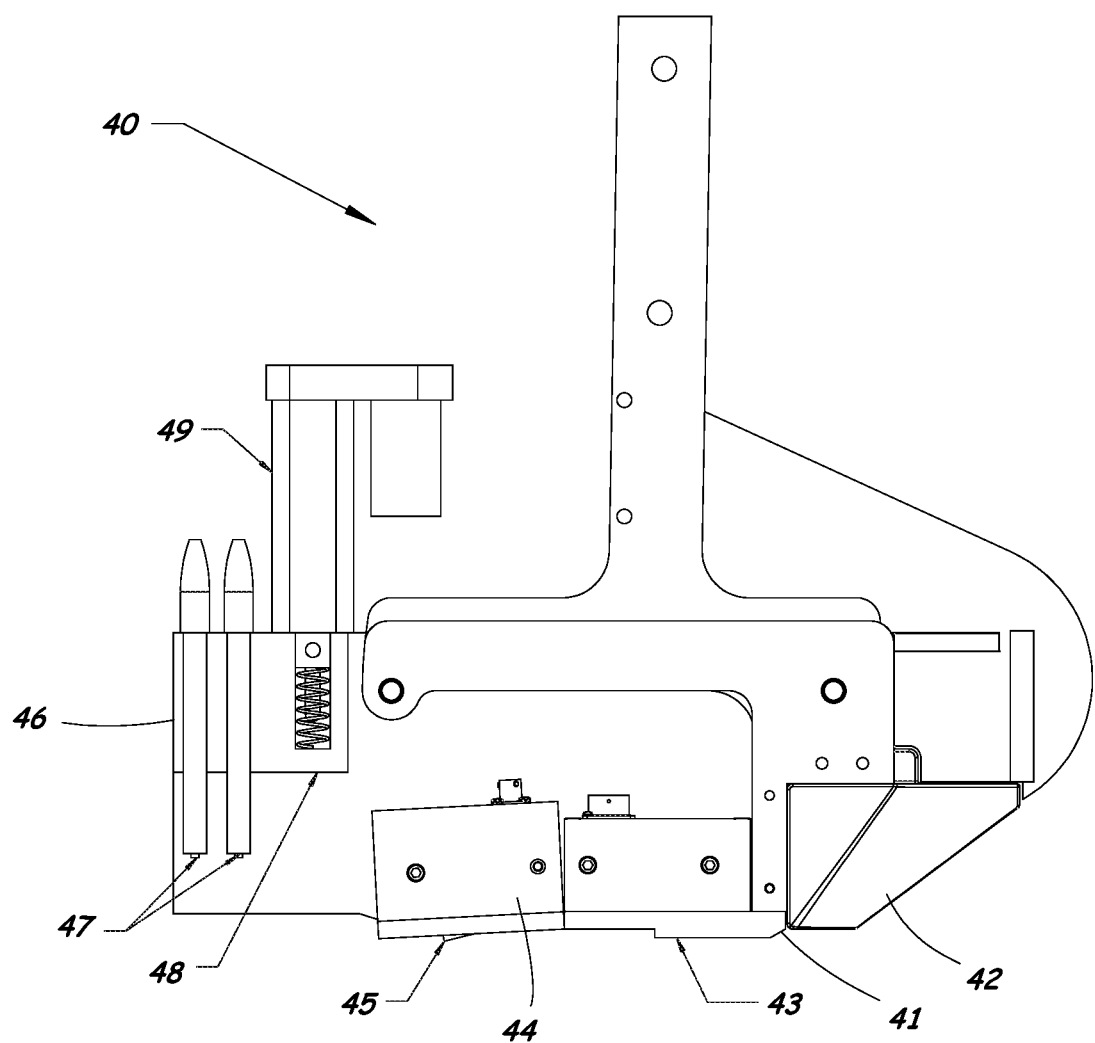
FIG. 8 is an elevation view of a runner having a pH sensor located behind the optical sensor and conductivity sensor for sensing soil pH according to a third embodiment of the present invention.
Figure 9:
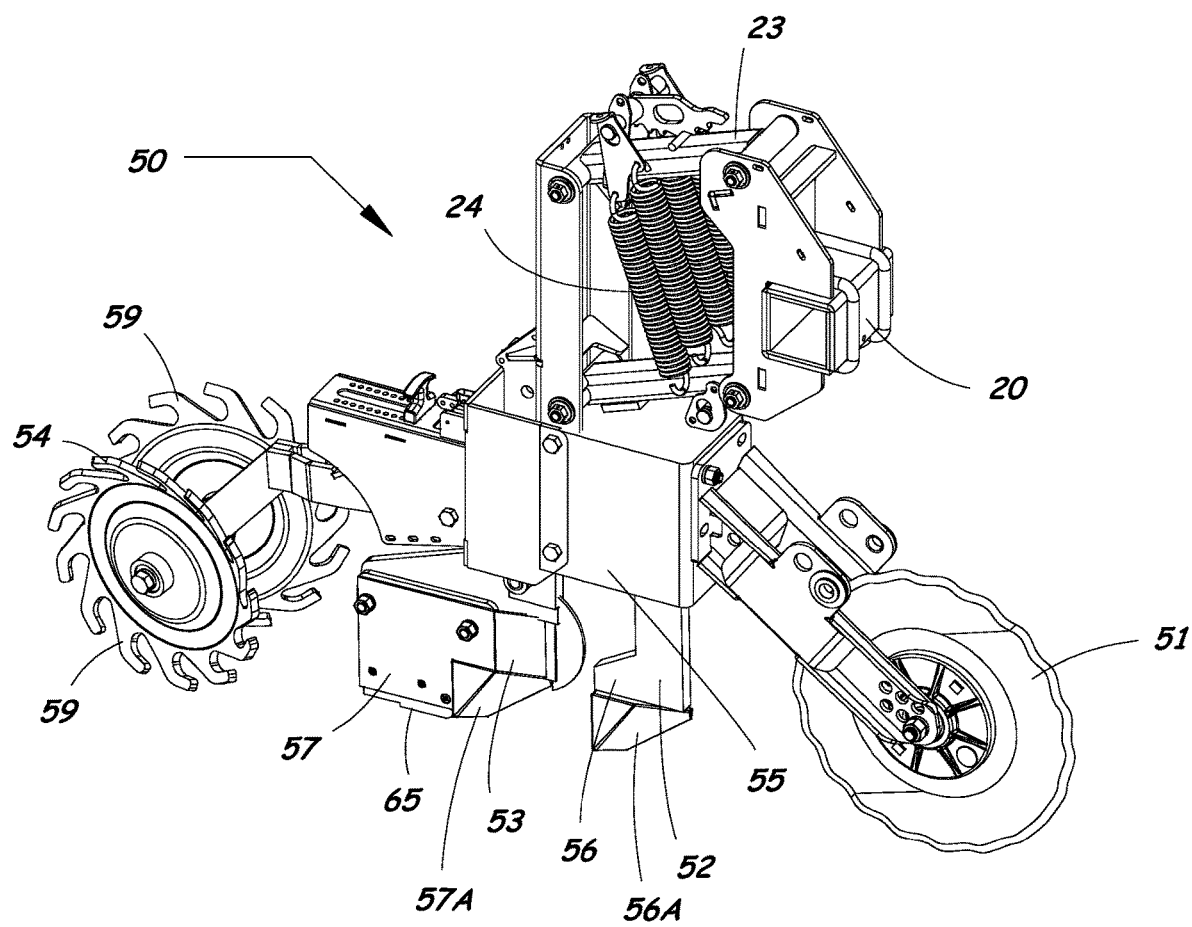
FIG. 9 is a front perspective view of a narrow profile sensor unit according to another embodiment of the present invention.
Figure 10:
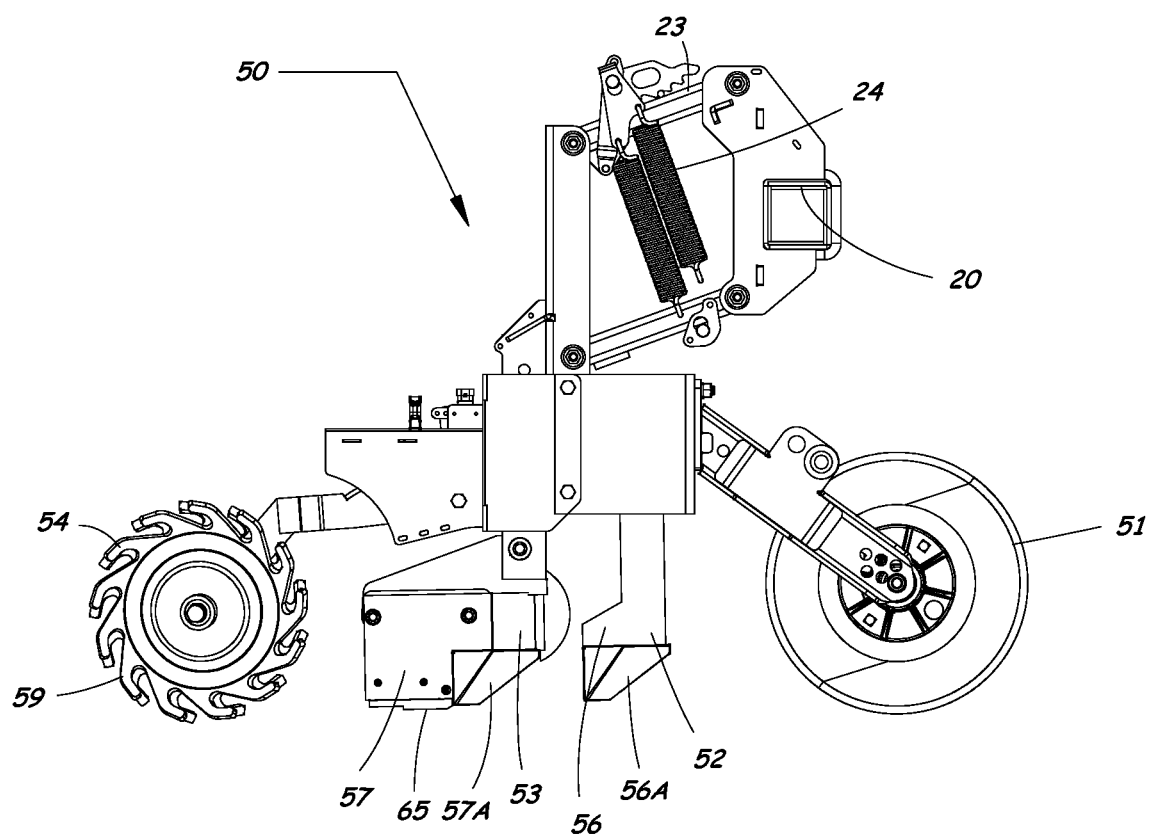
FIG. 10 is a side elevation view of the narrow profile sensor unit shown in FIG. 9.
Figure 11:
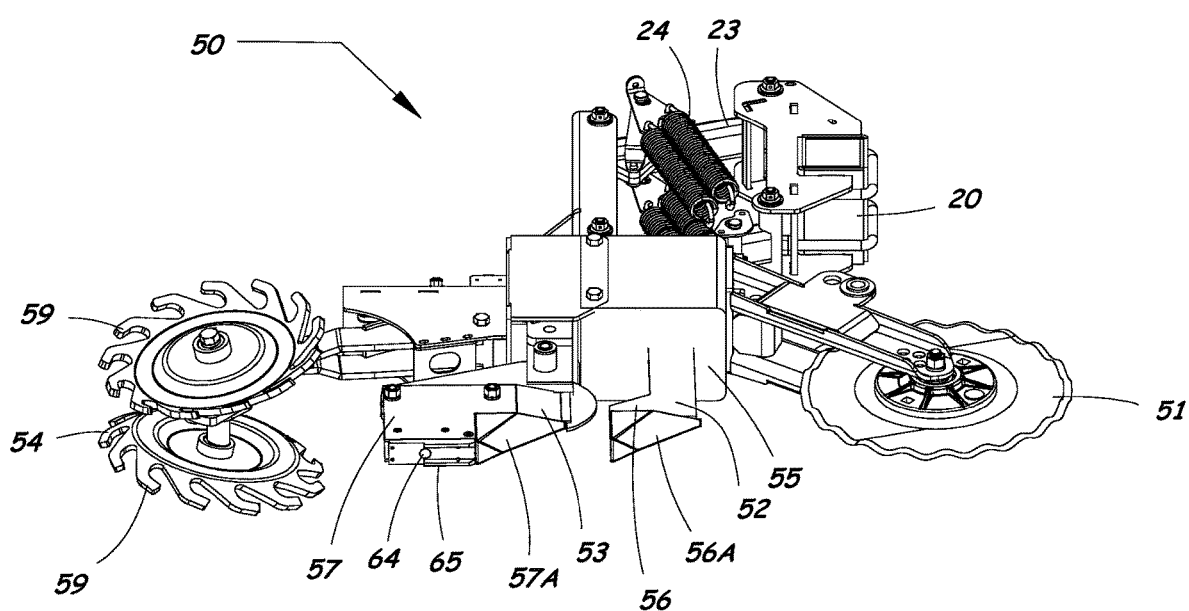
FIG. 11 is a lower right side perspective view of the narrow profile sensor unit shown in FIG. 9.
Figure 12:
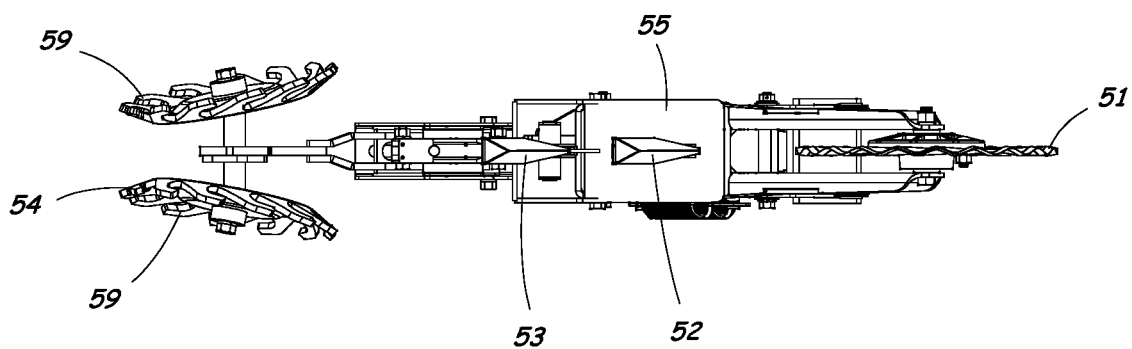
FIG. 12 is a bottom view of the narrow profile sensor unit shown in FIG. 9.

FIG. 8 shows a system for measuring pH of soil in a field incorporated into a runner 40 suitable for use in the narrow profile sensor unit 11. A front portion 41 of the runner 40 includes leading edge 42, an optical sensor module 43 with an optical window positioned in a bottom surface of the runner 40, and a conductivity sensor module 44 with one or more electrodes 45 positioned behind the optical sensor module 43 for sliding contact with the soil in the slot. The electrode 45 has an angled leading edge that slopes downwardly and rearwardly to provide better soil contact.

A pH sensor 46 having at least one ion selective electrode 47 is attached to a rear portion of the runner 40 behind the conductivity sensor module 44. The pH sensor 46 in the illustrated embodiment includes a pair of ion-selective electrodes 47, an electrode holder 48, and a linear actuator 49 for lowering the electrodes 47 into contact with the soil in the bottom of the slot opened by the front portion 41 of the runner 40.

In use, the pH sensor 46 can be lowered into contact with the soil in the bottom of the slot when the implement is stopped. The pH sensor 46 collects a pH measurement of the soil in situ. The runner 40 can also be used to collect soil reflectance data using the optical sensor module 43, and to collect soil electrical conductivity data or soil moisture data using the conductivity sensor module 44. The soil reflectance measurements and soil electrical conductivity measurements are collected on-the-go while the implement is traversing the field, while the pH measurements are collected when the implement is stopped at predetermined locations in the field.

FIGS. 9 to 12 show a narrow profile sensor unit 50 according to another embodiment of the invention. The narrow profile sensor unit 50 includes a first soil engaging component 51, a second soil engaging component 52, a third soil engaging component 53, and a fourth soil engaging component 54. The first, second, third and fourth soil engaging components 51, 52, 53, 54 are arranged substantially in-line with each other so that the second, third and fourth soil engaging components 52, 53, 54 follow behind the first soil engaging component 51 during forward movement of the implement through the field. The narrow profile sensor unit 50 is substantially the same as the narrow profile sensor unit 11 of the embodiment described above, except that the second, third and fourth soil engaging components 52, 53, 54 are different.

The first soil engaging component 51 shown in FIGS. 9 to 12 is a rotating coulter 51 arranged to open a slot in the soil. The second and third soil engaging components 52, 53 are part of a runner assembly 55 having a leading shank 56 and a runner 57 arranged to follow behind the leading shank 56. The leading shank 56 has a replaceable soil engaging wear plate 56A and is arranged to follow behind the first soil engaging component 51 for sliding contact with the soil in the slot created by the first soil engaging component 51. The runner 57 has a replaceable soil engaging wear plate 57A and is arranged to follow behind the leading shank 56 for sliding contact with the soil in the slot behind the leading shank 56. The wear plates 56A, 57A can be made of a material having a high wear resistance, such as chromium carbide.

The fourth soil engaging component 54 in the illustrated embodiment is a pair of spoked wheels 59 arranged to follow behind the runner 57 to close the slot.

In the embodiment shown in FIGS. 9 to 12, the first, second, third and fourth soil engaging components 51, 52, 53, 54 of the narrow profile sensor unit 50 provide a four electrode array for measuring soil electrical conductivity. The electrode array includes the first soil engaging component 51 functioning as the first electrode for contacting the soil. Second and third electrodes of the electrode array are the leading shank 56 and the runner 57 and their respective wear plates 56A, 57A. One of the spoked wheels 59 of the fourth soil engaging component 54 functions as the fourth electrode of the electrode array. Various signal processing circuits can be used with the electrode array, similar to the first embodiment described above.

The narrow profile sensor unit 50 is also equipped with other sensors for measuring soil properties. The runner 57 includes an optical window 64 in the lower soil engaging surface. A sensor for measuring optical reflectance of the soil through the optical window 64 is contained within the runner 57. A pair of protective fins 65 are positioned on right and left sides of the optical window 64 and protrude from the runner 57 below a lower surface of the optical window 64 for protecting the window 64 during use.

FIG. 13 illustrates a narrow profile sensor unit 70, which is substantially the same as the unit 50 shown in FIGS. 9 to 12, except that the first soil engaging component is a rotating disk 71 instead of a coulter.

An agricultural implement having a primary function of tillage, planting or fertilizing, can be equipped with the measurement systems of the present invention to provide a secondary function of measuring and mapping soil properties.

Figure 14:
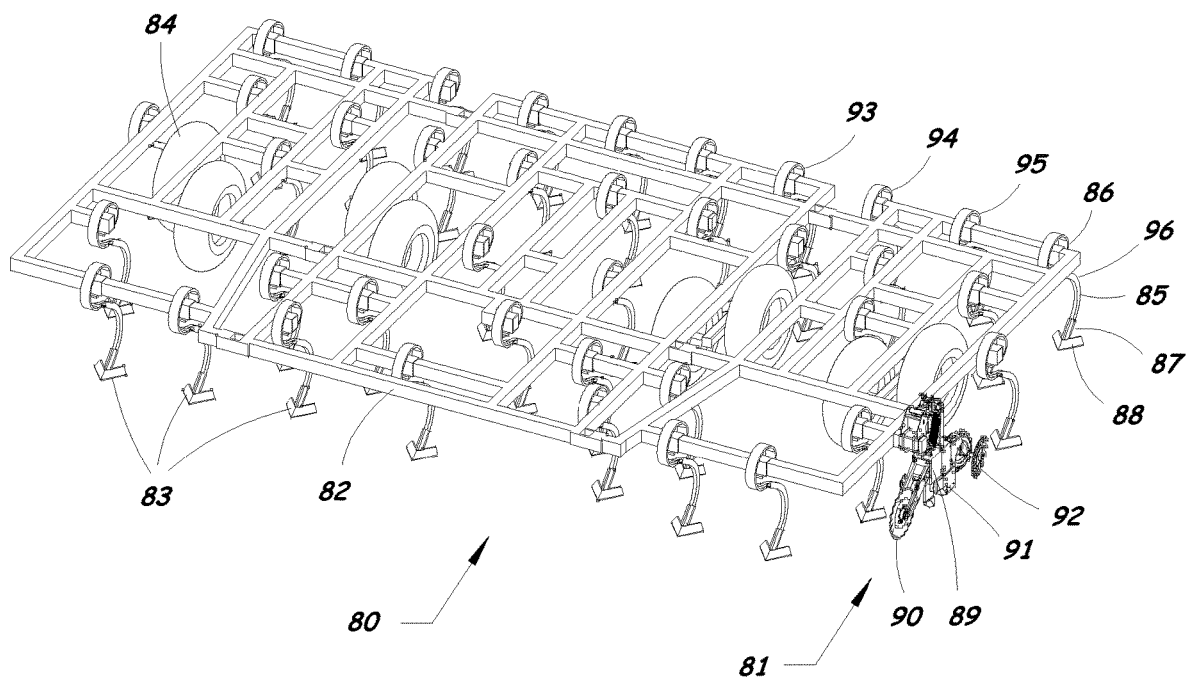
FIG. 14 is a perspective view of a field cultivator equipped with a narrow profile sensor unit of the present invention.

FIGS. 14 to 17 illustrate a field cultivator 80 equipped with a soil conductivity measurement system 81 according to the present invention. As shown in FIG. 14, the field cultivator 80 includes a frame 82, a plurality of sweep assemblies 83 spaced across a width of the implement 80 and attached to the frame 82, and a plurality of wheels 84 for supporting the implement 80 during transport and for gauging an operating depth during tillage operations. The sweep assemblies 83 each include a spring shank 85 having one end 86 attached to the frame 82 and a lower end 87 with a sweep 88 or other tillage tool attached thereto for tilling soil.

A narrow profile sensor unit 89 is attached to the frame 82 of the field cultivator 80 for measuring soil properties, such as shallow soil conductivity, soil temperature, soil moisture, soil reflectance, and soil pH. The narrow profile sensor unit 89 can have the same construction and function as the narrow profile sensor unit 11 described above and illustrated in FIGS. 3 to 13. The narrow profile sensor unit 89 includes a front disk or coulter 90 arranged to open a slot in the soil, a runner assembly 91 arranged to follow behind the front disk or coulter 90 for sliding contact with the soil in the slot, and a rotating disk or a spoked wheel 92 arranged to follow behind the runner assembly 91 to close the slot. An array of four electrodes is provided by the front disk or coulter 90 as a first electrode, protrusions on the runner assembly 91 as second and third electrodes, and the rotating disk or spoked wheel 92 as a fourth electrode. The runner assembly 91 has an optical window, and the sensor unit 89 includes a sensor for measuring optical reflectance of soil through the optical window.

Figure 15:
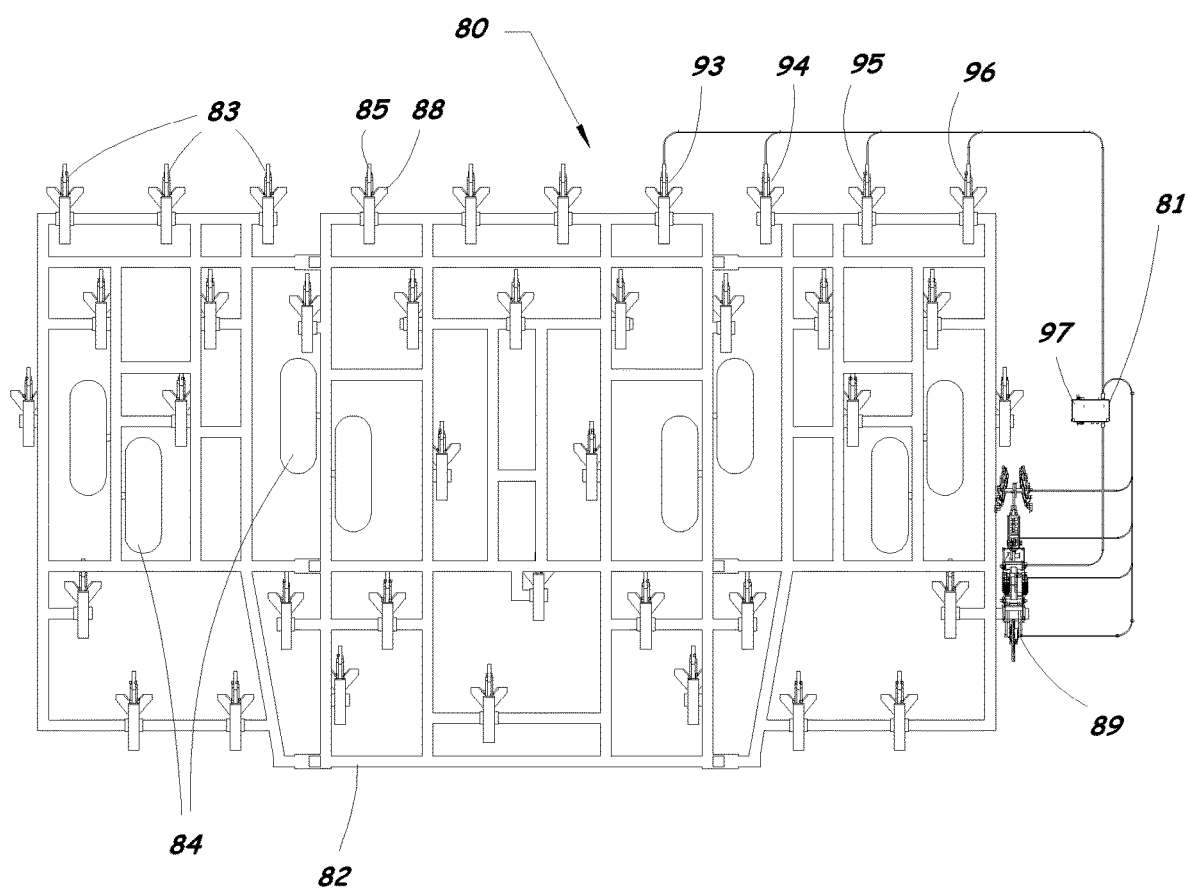
FIG. 15 is a plan view of the field cultivator shown in FIG. 14, with four of the cultivator sweeps being used as soil-engaging electrodes for a soil conductivity measurement system.

The plurality of sweep assemblies 83 include an array of four sweep assemblies 93-96 that are used to measure soil conductivity at a relatively deep depth in the soil. The four sweep assemblies 93-96 have electrically insulated cultivator sweeps or electrically insulated attachments to the shanks on which the cultivator sweeps are mounted. As illustrated in FIG. 15, these four sweep assemblies 93-96 are positioned across the rear of the frame 82. However, other configurations are also possible, such as four sweep assemblies positioned across the front of the frame, or four sweep assemblies positioned along a diagonal line on the frame. The four sweep assemblies 93-96 forming the array are placed in alignment with each other, but the alignment can be in a lateral direction, a longitudinal direction, or a diagonal direction. The four sweep assemblies 93-96 forming the array provide the same tillage function as the other sweep assemblies 83 of the field cultivator 80.

The four sweep assemblies 93-96 include a first pair of soil-engaging electrodes mounted to or integral with the corresponding sweep assemblies 93 and 96, and a second pair of soil-engaging electrodes mounted to or integral with the corresponding sweep assemblies 94, 95 between the first pair of soil-engaging electrodes 93, 96. The first and second pairs of electrodes 93-96 are electrically insulated from each other and from the frame 83. A controller 97 on the implement 80 includes a soil conductivity measurement system that passes a current between the first pair of soil-engaging electrodes through the soil and measures a voltage resulting from the current between the second pair of soil-engaging electrodes to determine soil conductivity.

Figure 16:
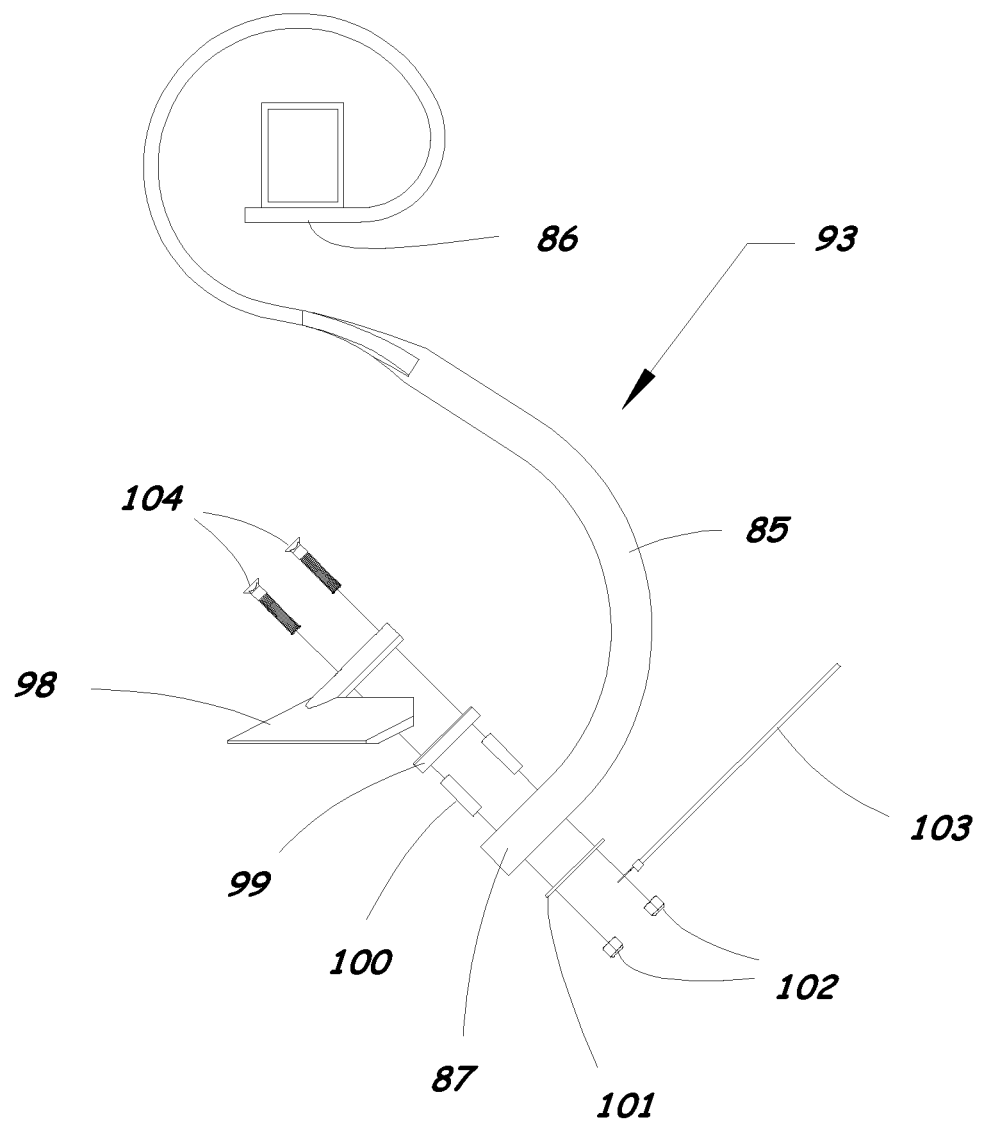
FIG. 16 is an exploded elevation view of a cultivator shank and sweep assembly showing the sweep electrically isolated from the shank.

FIG. 16 illustrates a sweep assembly 93 having an electrically isolated sweep 98. A sweep insulator 99 is placed between the sweep 98 and the shank 85, bolt insulator sleeves 100 are placed in the mounting holes in the shank 85, and a nut insulator 101 is placed between the mounting nuts 102 and the shank 85. The sweep insulator 99, bolt insulator sleeves 100, and nut insulator 101 prevent any metal-to-metal contact between the sweep 98 and the shank 85, thereby allowing the sweep 98 to function as a soil-engaging electrode 98. A signal wire 103 can be attached to one of the mounting bolts 104 for passing a current to the sweep 98 or measuring a voltage at the sweep 98.

Figure 17:
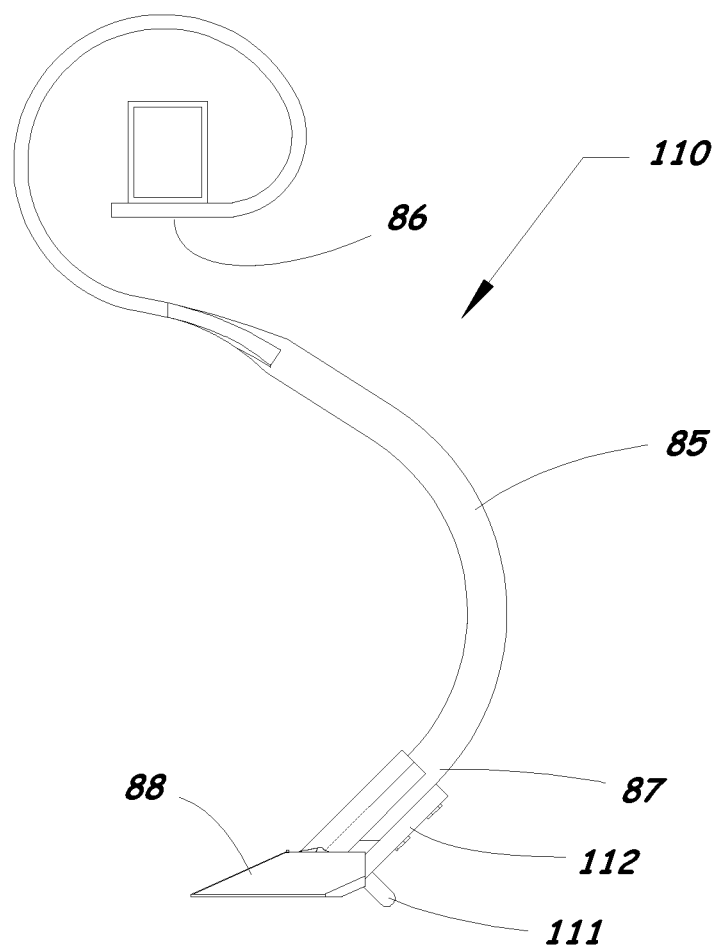
FIG. 17 is an elevation view of a cultivator shank and sweep assembly with an electrode protruding rearwardly and downwardly from the sweep.

To aid in signal strength and for simpler isolation, an additional soil-engaging component can be added to the shank 85 of the implement. For example, FIG. 17 illustrates a sweep assembly 110 having an electrically insulated electrode 111 attached to the lower end 87 of the shank 85. A nylon insulator block 112 can be used to attach the electrode 111 to the lower end 87 of the shank 85 using the existing mounting bolts 104 for the sweep 98. The electrode 111 can be, for example, a carbide electrode that protrudes downwardly and rearwardly from the lower end 87 of the shank 85.

By using the four electrically isolated soil-engaging electrodes 98, 111 on four existing sweep assemblies 93-96 on the field cultivator 80, soil conductivity can be measured by the implement while performing normal tillage operations, thereby saving an extra trip over the field. The spacing of the soil-engaging electrodes 98, 111 provides a relatively deep soil conductivity measurement (e.g., approximately three to six feet in depth), while the spacing of the electrodes on the narrow profile sensor unit 89 provides a relatively shallow soil conductivity measurement (e.g., less than three feet in depth). Various other soil properties, such as soil temperature, soil reflectance, soil moisture, and soil pH, can also be measured by the implement using the narrow profile sensor unit 89 while performing normal tillage operations.

The electronic controller 97 on the field cultivator 80 generates the electrical signal, conditions and processes the conductivity measurements, performs the analog-to-digital conversion, matches the electrical conductivity readings with GPS positions, and communicates the georeferenced electrical conductivity data to a datalogging device.

Figure 18:
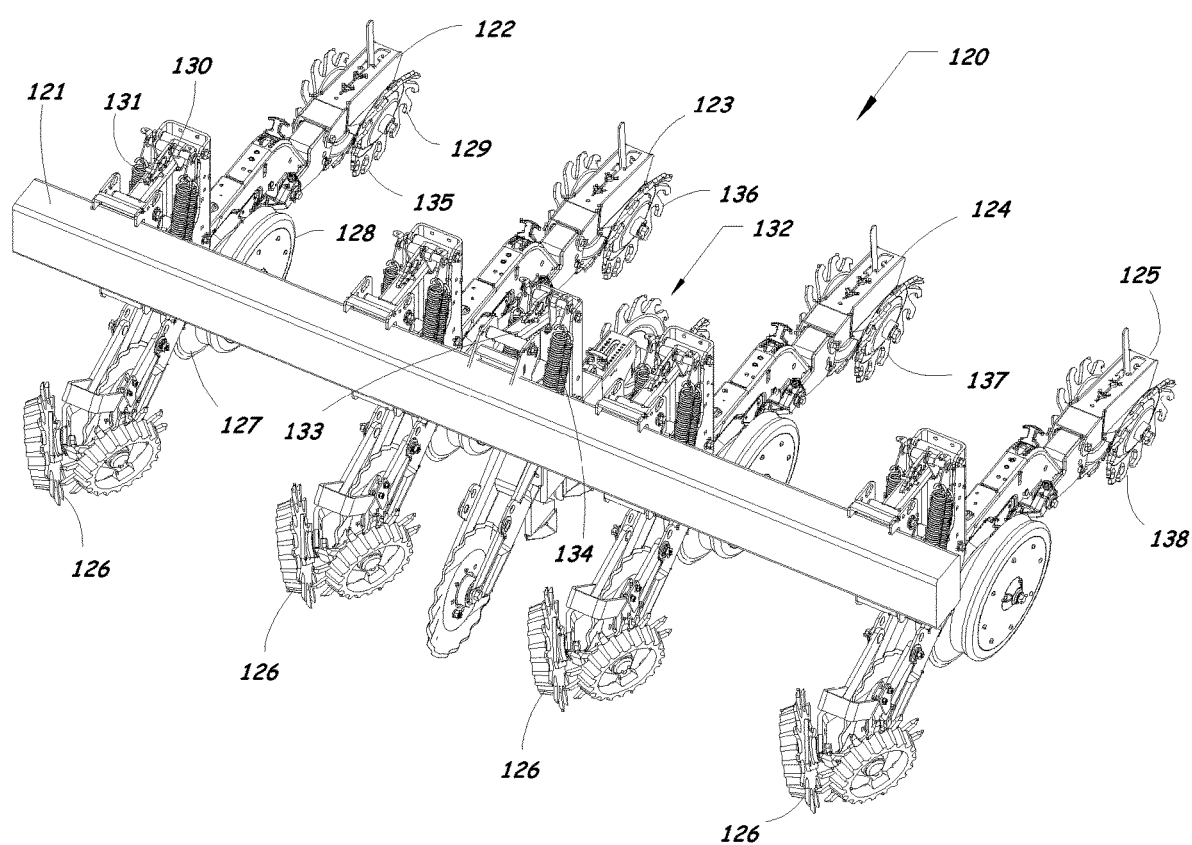
FIG. 18 is a perspective view of a row crop planter having four row units attached to a toolbar, and a narrow profile sensor unit attached between two adjacent row units.
Figure 19:
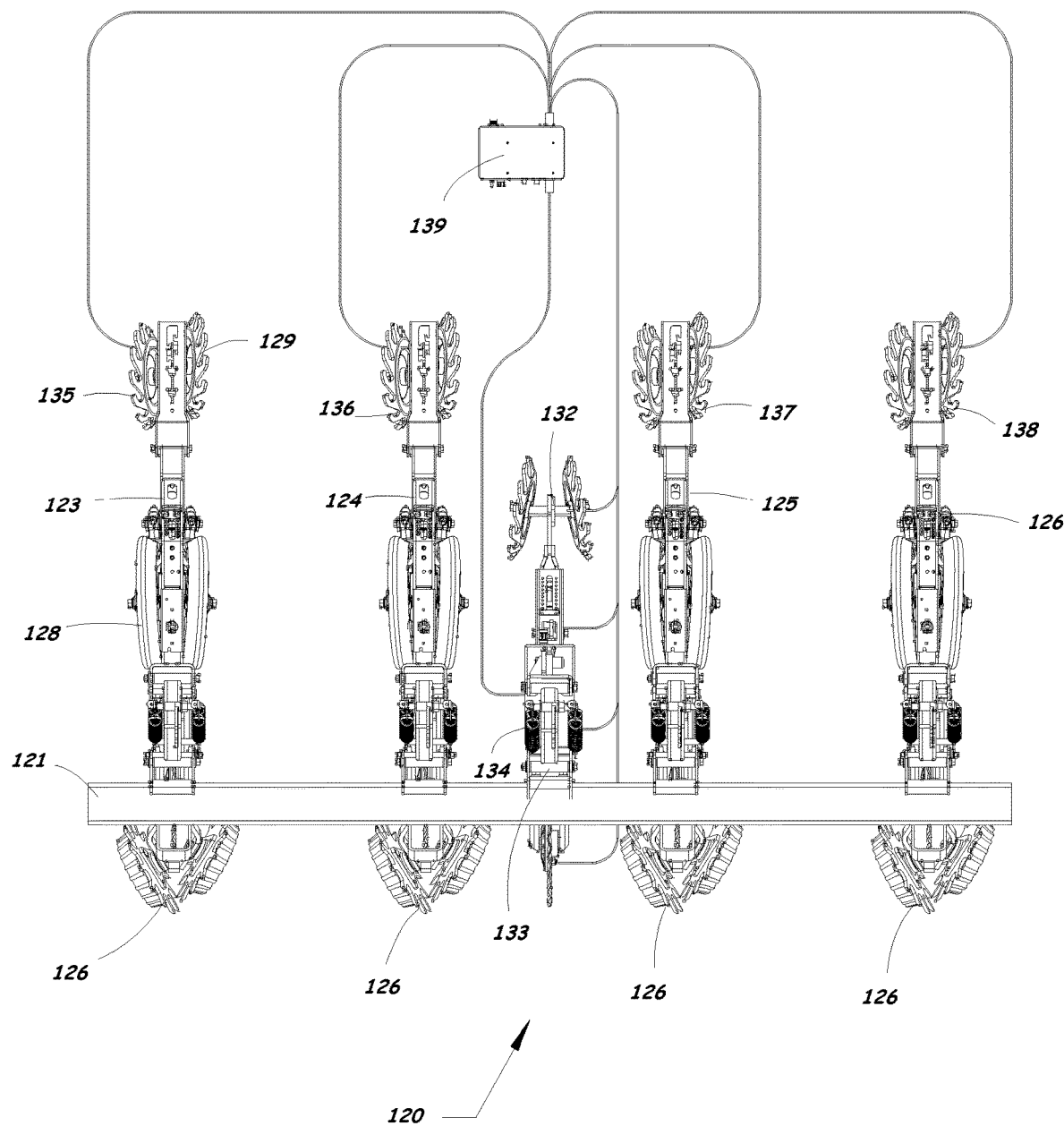
FIG. 19 is a plan view of the row crop planter shown in FIG. 18, with four of the closing wheels on the planter row units being used as soil-engaging electrodes for a soil conductivity measurement system.

FIGS. 18 and 19 illustrate a row crop planter 120 equipped with a soil conductivity measurement system according to the present invention. As shown in FIG. 18, the row crop planter 120 includes a toolbar 121, and a plurality of planter row units 122-125 attached to the toolbar 121. The planter row units 122-125 each include a row clearing assembly 126, a furrow opener assembly 127 with gauge wheels 128, and a furrow closing assembly 129. The planter row units 122-125 are attached to the toolbar 121 by parallel linkage assemblies 130. Springs 131 are attached to the parallel linkage assemblies 130 to transfer additional down pressure from the toolbar 121 to the row units 122-125.

A narrow profile sensor unit 132 is attached to the same toolbar 121 as the planter row units 122-125 using a similar parallel linkage assembly 133 and springs 134 for transferring additional down pressure from the toolbar 121 to the sensor unit 132. This allows the implement 120 to be used for its original purpose of planting, as well as for measuring various properties of the soil in the field. The narrow profile sensor unit 132 can be used for measuring soil properties, such as shallow soil conductivity, soil temperature, soil moisture, soil reflectance, and soil pH. The narrow profile sensor unit 132 can have the same construction and function as the narrow profile sensor unit 11 described above and illustrated in FIGS. 3 to 13.

The planter 120 includes four row units 122-125 that provide an array of four soil-engaging electrodes 135-138. The soil-engaging electrodes 135-138 can be the row cleaner 126 or coulter device on the front of each row unit, the closing wheels 129 on the back of each row unit, or the entire planter row unit can serve as one of the electrodes. The soil-engaging electrodes are electrically insulated from each other and from the toolbar 121 or other parts of the planter 120 so that they can be used effectively to pass a current into the soil and to measure a voltage resulting from the current.

In order to serve as an electrode, the soil-engaging component needs to be electrically isolated from other components of the implement. On soil-engaging components such as wheels or disks 129 that use bearings to provide rotation, a commutator or similar constant contact device is used to maintain electrical signal continuity.

As illustrated in FIG. 19, the four soil-engaging electrodes 135-138 of the planter row units 122-125 can be the closing wheels 129 on four adjacent row units of the planter 120. The four soil-engaging electrodes 135-138 include a first pair of soil-engaging electrodes 135, 138 mounted to or integral with the outer pair of row units 122, 125, and a second pair of soil-engaging electrodes 136, 137 mounted to or integral with the inner pair of row units 123, 124 between the outer pair of row units 122, 125. The first and second pairs of electrodes 135-138 are electrically insulated from each other and from the toolbar 121. A controller 139 on the planter 120 includes a soil conductivity measurement system that passes a current between the first pair of soil-engaging electrodes 135, 138 through the soil and measures a voltage resulting from the current between the second pair of soil-engaging electrodes 136, 137 to determine soil conductivity.

The electronic controller 139 on the planter 120 generates the electrical signal, conditions and processes the conductivity measurements, performs the analog-to-digital conversion, matches the electrical conductivity readings with GPS positions, and communicates the georeferenced electrical conductivity data to a datalogging device.

By using four electrically isolated soil-engaging components 129 on four existing planter row units 122-125 on the planter 120, soil conductivity can be measured by the planter 120 while performing normal planting operations, thereby saving an extra trip over the field. The spacing of the soil-engaging electrodes 135-138 provides a relatively deep soil conductivity measurement (e.g., approximately three to six feet in depth), while the spacing of the electrodes on the narrow profile sensor unit 132 provides a relatively shallow soil conductivity measurement (e.g., less than three feet in depth). Various other soil properties, such as soil temperature, soil reflectance, soil moisture, and soil pH, can also be measured by the planter 120 using the narrow profile sensor unit 132 while performing normal planting operations.

The present invention provides a system and method for equipping and using existing agricultural implements to measure soil electrical conductivity using existing soil-engaging components as electrodes.

Because of the spacing of soil-engaging components on most farm implements and the need for classic electrical conductivity arrays to be based on in-line electrode placement, the soil-engaging electrodes may be several feet apart, resulting in an electrical conductivity reading of three or more feet in depth. Having two electrical conductivity arrays (e.g., one array provided by the existing soil-engaging components, and another array provided by the narrow profile sensor unit), soil electrical conductivity measurements of the topsoil and the subsoil can be acquired simultaneously.

While the invention has been described in connection with specific embodiments thereof, it is to be understood that this is by way of illustration and not of limitation, and the scope of the appended claims should be construed as broadly as the prior art will permit.

What is claimed is:

1. An agricultural implement having a secondary function of measuring soil conductivity, comprising:

a frame or toolbar adapted to be conveyed over a ground surface;

a plurality of soil-engaging components mounted to the frame or toolbar, said soil-engaging components being spaced across a width of the implement to provide a tillage, planting or fertilizing function;

first and second pairs of soil-engaging electrodes mounted to or integral with corresponding first and second pairs of said soil-engaging components, said second pair of electrodes being arranged between and aligned with said first pair of electrodes, said first and second pairs of electrodes being electrically insulated from each other and from said frame; and a soil conductivity measurement system that passes a current between the first pair of soil-engaging electrodes through the soil and measures a voltage resulting from the current between the second pair of soil-engaging electrodes to determine soil conductivity;

wherein said implement is a field cultivator and said plurality of soil-engaging components comprise cultivator sweeps; and wherein said first and second pairs of electrodes are electrically insulated cultivator sweeps or electrically insulated attachments to shanks on which cultivator sweeps are mounted, and said field cultivator further comprises a plurality of non-electrically insulated cultivator sweeps, wherein said non-electrically insulated cultivator sweeps and said cultivator sweeps that are electrically insulated or have electrically insulated attachments are spaced across a width of the implement to provide a primary function of tillage, while said cultivator sweeps that are electrically insulated or have electrically insulated attachments provide the secondary function of measuring soil conductivity in addition to the primary function of tillage.

2. The agricultural implement according to claim 1, further comprising a narrow profile sensor unit attached to said frame for measuring at least one soil property in addition to the soil conductivity measured by said soil conductivity measurement system using said first and second pairs of soil-engaging electrodes.

3. The agricultural implement according to claim 1, further comprising an additional sensor unit attached to said frame or toolbar, said sensor unit being separate from said first and second pairs of soil-engaging electrodes and comprising a sensor for sensing at least one of soil temperature, soil reflectance, soil moisture, and soil pH.

4. The agricultural implement according to claim 3, wherein said additional sensor unit comprises a sensor for sensing at least one of soil moisture and soil pH.

5. An agricultural implement having a secondary function of measuring soil conductivity, comprising:
a frame or toolbar adapted to be conveyed over a ground surface;
a plurality of soil-engaging components mounted to the frame or toolbar, said soil-engaging components being spaced across a width of the implement to provide a tillage, planting or fertilizing function;
first and second pairs of soil-engaging electrodes mounted to or integral with corresponding first and second pairs of said soil-engaging components, said second pair of electrodes being arranged between and aligned with said first pair of electrodes, said first and second pairs of electrodes being electrically insulated from each other and from said frame; and
a soil conductivity measurement system that passes a current between the first pair of soil-engaging electrodes through the soil and measures a voltage resulting from the current between the second pair of soil-engaging electrodes to determine soil conductivity;
wherein said implement is a field cultivator and said plurality of soil-engaging components comprise cultivator sweeps;
wherein said first and second pairs of electrodes are electrically insulated cultivator sweeps or electrically insulated attachments to shanks on which cultivator sweeps are mounted, and said field cultivator further comprises a plurality of non-electrically insulated cultivator sweeps for performing tillage operations;
further comprising a narrow profile sensor unit attached to said frame for measuring at least one soil property in addition to the soil conductivity measured by said soil conductivity measurement system using said first and second pairs of soil-engaging electrodes; and
wherein said narrow profile sensor unit comprises an electrode array for measuring soil conductivity at a shallower depth than the soil conductivity measured by said soil conductivity measurement system using said first and second pairs of soil-engaging electrodes.

6. The agricultural implement according to claim 5, wherein said narrow profile sensor unit comprises a front disk or coulter arranged to open a slot in the soil, a runner assembly arranged to follow behind said front disk or coulter for sliding contact with the soil in said slot, and a rotating disk or a spoked wheel arranged to follow behind said runner to close said slot.

7. The agricultural implement according to claim 6, wherein said front disk or coulter is a first electrode of said electrode array, said runner assembly comprises second and third electrodes of said electrode array, and said rotating disk or spoked wheel comprises a fourth electrode of said electrode array.

8. The agricultural implement according to claim 7, wherein said electrode array is a Wenner or Schlumberger array with said first and fourth electrodes connected to a source of electrical current and said second and third electrodes connected to a voltage measuring circuit.

9. The agricultural implement according to claim 8, wherein said runner assembly comprises an optical window, and said narrow profile sensor unit comprises a sensor for measuring optical reflectance of soil through said optical window.

10. An agricultural implement having a secondary function of measuring soil conductivity, comprising:
a frame or toolbar adapted to be conveyed over a ground surface;
a plurality of soil-engaging components mounted to the frame or toolbar, said soil-engaging components being spaced across a width of the implement to provide a tillage, planting or fertilizing function;
first and second pairs of soil-engaging electrodes mounted to or integral with corresponding first and second pairs of said soil-engaging components, said second pair of electrodes being arranged between and aligned with said first pair of electrodes, said first and second pairs of electrodes being electrically insulated from each other and from said frame; and
a soil conductivity measurement system that passes a current between the first pair of soil-engaging electrodes through the soil and measures a voltage resulting from the current between the second pair of soil-engaging electrodes to determine soil conductivity;
wherein said implement is a row crop planter having a plurality of planter row units mounted to a toolbar, and said plurality of soil-engaging electrodes comprise soil-engaging components of four of said planter row units which are electrically isolated from each other, wherein said plurality of planter row units provide a primary function of planting, while said soil-engaging electrodes of said planter row units provide the secondary function of measuring soil conductivity.

11. The agricultural implement according to claim 10, wherein said soil-engaging components of said four planter row units comprise closing wheels of said four row units, which are electrically insulated from each other.

12. The agricultural implement according to claim 10, wherein said soil-engaging components of said four planter row units comprise row cleaner or coulter devices on a front of said four row units, which are electrically insulated from each other.

13. The agricultural implement according to claim 10, wherein each soil-engaging electrode comprises one of said planter row units, which is electrically insulated from the other planter row units.

14. The agricultural implement according to claim 10, further comprising a narrow profile sensor unit attached to said toolbar for measuring at least one soil property in addition to the soil conductivity measured by said soil conductivity measurement system using said first and second pairs of soil-engaging electrodes.

15. The agricultural implement according to claim 10, further comprising an additional sensor unit attached to said toolbar, said sensor unit being separate from said first and second pairs of soil-engaging electrodes and comprising a sensor for sensing at least one of soil temperature, soil reflectance, soil moisture, and soil pH.

16. The agricultural implement according to claim 15, wherein said additional sensor unit comprises a sensor for sensing at least one of soil moisture and soil pH.

17. An agricultural implement having a secondary function of measuring soil conductivity, comprising:
- a frame or toolbar adapted to be conveyed over a ground surface;
- a plurality of soil-engaging components mounted to the frame or toolbar, said soil-engaging components being spaced across a width of the implement to provide a tillage, planting or fertilizing function;
- first and second pairs of soil-engaging electrodes mounted to or integral with corresponding first and second pairs of said soil-engaging components, said second pair of electrodes being arranged between and aligned with said first pair of electrodes, said first and second pairs of electrodes being electrically insulated from each other and from said frame; and
- a soil conductivity measurement system that passes a current between the first pair of soil-engaging electrodes through the soil and measures a voltage resulting from the current between the second pair of soil-engaging electrodes to determine soil conductivity;
- wherein said implement is a row crop planter having a plurality of planter row units mounted to a toolbar, and said plurality of soil-engaging electrodes comprise soil-engaging components of four of said planter row units; further comprising a narrow profile sensor unit attached to said toolbar for measuring at least one soil property in addition to the soil conductivity measured by said soil conductivity measurement system using said first and second pairs of soil-engaging electrodes; and
- wherein said narrow profile sensor unit comprises an electrode array for measuring soil conductivity at a shallower depth than the soil conductivity measured by said soil conductivity measurement system using said first and second pairs of soil-engaging electrodes.

18. The agricultural implement according to claim 17, wherein said narrow profile sensor unit comprises a front disk or coulter arranged to open a slot in the soil, a runner assembly arranged to follow behind said front disk or coulter for sliding contact with the soil in said slot, and a rotating disk or a spoked wheel arranged to follow behind said runner to close said slot.

19. The agricultural implement according to claim 18, wherein said front disk or coulter is a first electrode of said electrode array, said runner assembly comprises second and third electrodes of said electrode array, and said rotating disk or spoked wheel comprises a fourth electrode of said electrode array.

20. The agricultural implement according to claim 19, wherein said electrode array is a Wenner or Schlumberger array with said first and fourth electrodes connected to a source of electrical current and said second and third electrodes connected to a voltage measuring circuit.

21. The agricultural implement according to claim 18, wherein said runner assembly comprises an optical window, and said narrow profile sensor unit comprises a sensor for measuring optical reflectance of soil through said optical window.

* * * * *